United States Patent [19]

Dreesman et al.

[11] Patent Number: 4,535,057
[45] Date of Patent: Aug. 13, 1985

[54] IMMUNOASSAY EMPLOYING MONOCLONAL HERPES SIMPLEX ANTIBODY AND BIOTIN-AVIDIN DETECTION SYSTEM

[75] Inventors: Gordon R. Dreesman, Houston, Tex.; Cynthia E. Kendall, Colombia, Mo.

[73] Assignee: AMF Incorporated, White Plains, N.Y.

[21] Appl. No.: 402,009

[22] Filed: Jul. 26, 1982

[51] Int. Cl.³ .......................................... G01N 33/54
[52] U.S. Cl. .................................... 435/5; 422/61; 435/7; 435/810; 436/510; 436/513; 436/531; 436/548; 436/808; 436/809
[58] Field of Search ................. 435/68, 172, 240, 241, 435/948, 5, 7, 810; 436/548, 510, 513, 531, 808, 809

[56] References Cited

U.S. PATENT DOCUMENTS

| | | |
|---|---|---|
| Re. 29,169 | 4/1977 | Schuurs . |
| 3,654,090 | 4/1972 | Schuurs et al. . |
| 3,839,153 | 10/1974 | Schuurs et al. . |
| 3,850,752 | 11/1974 | Schuurs et al. . |
| 3,879,262 | 4/1975 | Schuurs et al. . |
| 4,016,043 | 4/1977 | Schuurs . |
| 4,152,411 | 5/1979 | Schall, Jr. . |
| 4,157,280 | 6/1979 | Halbert et al. . |
| 4,228,237 | 10/1980 | Hevey et al. . |
| 4,271,145 | 6/1981 | Wands .................. 435/948 X |
| 4,292,403 | 9/1981 | Duermeyer . |
| 4,298,685 | 11/1981 | Parikh et al. . |
| 4,430,437 | 2/1984 | Hampar ................ 435/172.2 X |

FOREIGN PATENT DOCUMENTS 2098730 11/1982 United Kingdom .

OTHER PUBLICATIONS

Brown, *Genetic Engineering News*, May–Jun. 1982.
Dreesman et al., *Intervirology*, 12: 115–119, (1979).
Guesdon et al., *J. of Histochem. and Cytochem.*, 27: 1131–1139, (1979).
Yolken, *Reviews of Infectious Diseases*, 4: 35–68, (1982).
"Lectins and Biotin-Avidin System"–1982; Vector Laboratories, Inc., Burlingame, Calif. 94010.
Wisdom, *Clinical Chemistry*, 22: 1243–1255, (1976).
Bayer et al., *FEBS Letters*, 68: 240–244, (1976).
Bayer et al., *TIBS* N–257–9, (Nov. 1978).
Heggeness et al., *J. of Cell. Bio.*, 73: 783–788, (1977).
Kennedy et al., *1982 FASEB Abstracts*–approx. Mar. 1982.
Zweig et al., *J. Virol.*, 32: 676–678.
Pereira et al., *Infection and Immunity*, 29: 724–732, (1980).
Eisenberg et al., *J. of Virology*, 41: 478–488, (1982).
Showalter et al., *Infection and Immunity*, 34: 684–692, (1981).
Zweig, *J. of Virology*, 35: 644–652, (1980).
Balachandran et al., *J. Clin. Microbiology*, 16: 205–208, (1982).
Pereira et al., *Infection and Immunity*, 35: 363–367, (1982).
Bayer et al., *J. of Histo. and Cytochem.*, 24: 933–939, (1976).
F. B. Hollinger et al., Jour. of Immunology, 107, 1099–1111, (1971).

*Primary Examiner*—Sidney Marantz
*Attorney, Agent, or Firm*—David E. Dougherty; Michael E. Zall

[57] ABSTRACT

An immunoassay and kit for determining a viral antigen, such as herpes simplex. In one embodiment, the antigen is immunocaptured by an insoluble matrix presenting IgG antibody against the viral antigen. The matrix resulting is subsequently contacted by biotin labeled monoclonal IgM antibody and labeled avidin.

18 Claims, 5 Drawing Figures

☆ = MONOCLONAL IgM - ANTI-HSV ANTIBODY

>● = BIOTIN LABELED ANTIBODY AGAINST, MOUSE IgM IMMUNOGLOBULIN

IMMUNOASSAY EMPLOYING MONOCLONAL HERPES SIMPLEX ANTIBODY AND BIOTIN-AVIDIN DETECTION SYSTEM

BACKGROUND OF THE INVENTION

Herpes viruses are composed of a DNA core surrounded by a icosahedral capsid and a lipoprotein envelope. These viruses have a special affinity for cells of ectodermal origin and tend to produce latent infections.

The herpes simplex viruses (HSV), which cause infections in humans, are herpes simplex virus type (HSV1) which causes primarily oral lesions, keratitis and encephalitis; and herpes simplex virus type 2 (HSV2) which causes primarily genital lesions and life threatening disease to newborns.

Genital HSV infections are primarily caused by HSV2, however, HSV1 can also cause venereal disease. It is thought that herpes is one of the most common sexually transmitted diseases.

The initial HSV infection is characterized by moderate to severely painful lesions, which often take the form of tiny blister-like sores, that can progress to ulcers. Initial infection may also be accompanied by nausea, headaches, and fever. The HSV infection may remain latent in the host and cause frequent recurrent infections. Fifty percent of infected individuals have recurrent episodes, whereas the other 50% do not. At the present time, there is no effective cure for any of the HSV infections.

It is estimated that the number of individuals with venereal HSV infections in the United States ranges from 5-40 million, with 20 million being the most commonly quoted figure. It is further estimated that approximately 300-500 thousand individuals per year are infected by HSV2.

HSV infections are usually not incapacitating to the adult. However, HSV infection of the fetus or newborn infant is a severe disease with a high mortality rate and serious secondary sequelae.

Venereal HSV infections are usually diagnosed by the appearance of lesions, cellular morphology, as demonstrated by PAP or Tzanck smear, direct or indirect immunofluorescent assays, or viral infectivity in tissue culture. The majority of herpes lesions are being diagnosed by the doctor or clinician based on the appearance of the lesion only.

It is difficult to determine if a genital lesion is caused by HSV. It is particularly difficult to diagnose herpes infections in females, since the characteristic blisters often break, resulting in an ulcerative lesion that looks similar to many other types of venereal lesions.

The Tzanck smear is often used to diagnose venereal herpes. However, a large amount of false negatives may be obtained. Both histological preparations (the Tzanck or PAP smear) have to be interpreted by a trained pathologist. However, even then, there is still a 20% chance of a false negative result.

Direct or indirect immunofluorescence detects the presence of HSV antigen in infected cells. The ability to detect the HSV antigen depends primarily on the quality of the specimen. The test can be difficult to read and interpret, therefore, whenever a negative result is obtained, a tissue cell culture should be inoculated with the specimen for verification.

At the present time, the only sure way to diagnose HSV infections is by growing the sample in a tissue cell culture. Definitive identification is then accomplished by an immunological procedure such as neutralization of the antigen by specific antibody or by a demonstraton of HSV virus antigens by the use of a specific antibody labeled with fluorescein isothiocyanate. This is probably the most common method for HSV identification, when the cost of and time for the test is not a consideration.

It is therefore highly desirable to have a diagnostic test of choice for identification of venereal HSV infections which is highly specific, very sensitive, able to be performed quickly (much faster than the current 2-10 day period), and available at a reasonable cost.

Such a test will be extremely useful in the screening and monitoring of pregnant women, the diagnosis of the HSV infected population who have recurrent infections, the diagnosis of new cases and the screening of individuals with herpes-like infections.

Immunoassays employing various reading modes have been described in the art. For a number of reasons, including the ease of reading and the level of skill required by the operator, enzyme immunoassay is often a method of choice, although fluorescent or radioactive markers or labels are also frequently employed.

As to one embodiment of this invention, in the diagnosis of an HSV infection, a particular serologic marker is of importance. The presence of specific antibody of the IgM immunoglobulin indicates that the patient has recently experienced an acute or primary infection, whereas IgG class antibody is characteristically observed in the blood during convalescence, or after the recurrent infections. Thus, a method for detecting IgM antibody is desirable.

Dreesman et al, *Intervirology*, 12: 115-119 (1979) describe a solid phase radioimmunoassay for HSV which measures type specific antibody for both HSV1 and HSV2.

Hollinger et al, *J. Immunol.* 107: 1099, (1971) describe a solid phase radioimmunoassay for the detection of hepatitis B surface antigen.

Hevey et al., U.S. Pat. No. 4,228,237 describee an insoluble phase enzyme immunoassay which employs enzyme labeled avidin and biotin labeled reagent (e.g. antibody) to detect a ligand (e.g. an antigen).

Parikh, U.S. Pat. No. 4,298,685 describes a diagnostic system where the biotin-avidin system is used to detect antigen by fixing avidin to form an insoluble phase which precipitates the biotin labeled competitive reaction product.

Guesdon et al, *J. Histochem. & Cytochem.* 27: 1131, (1979) describe the use of biotin labeled antibody followed by the used of avidin labeled enzyme in an immunoassay. The reference likewise describes the use of avidin as a linking agent between biotin labeled antibody and biotin labeled enzyme.

Bayer et al, November 1978 TIBS pp. N257-N252 and Bayer et al, FEBS Letters October 1976 Vol. 68, No. 2, discuss the avidin biotin complex in Microbiology.

Wands et al, Proceedings in the National Academy of Sciences, U.S.A., Vol. 78, pp. 1214-1218 (1981), and U.S. Pat. No. 4,271,145 describe the use of high affinity IgM monoclonal antibody in the immunodiagnosis of hepatitis B virus.

Wisdom, *Clin. Chem.* Vol. 22 pp. 1243-1255 (1976) and Yolken, *Rev. Infect. Diseases*, 4: 35-68, (1982) discuss enzyme immunoassays in review articles.

A number of patents relating to enzyme immunoassays by Schuurs and co-workers is disclosed in U.S. Pat. Nos. 3,654,090, 3,791,932, 3,850,752, 3,839,153 and 3,879,262, 4,106,043 and Re 29,169.

The use of polyclonal antisera to characterize HSV1 and HSV2 has demonstrated extensive serological cross-reactivity between the two serotypes of virus. Hyperimmune sera produced against one HSV type will generally neutralize the heterologous type, although to a lesser degree. Using sensitive radioimmunoassays and experimentally produced monospecific antisera, both type-common and type-specific HSV antigenic determinants have been demonstrated. With the advent of procedures for producing monoclonal antibodies, specific determinants present as a single antigenic site could be characterized, thus facilitating the serological detection of HSV cross-reacting and type-specific antigens. Certain monoclonal antibodies against HSV-coded proteins have been described and have detected both type-common and type-specific HSV-antigenic determinants. However, prior to the invention herein, it is believed that monoclonal IgM antibody against HSV was unknown.

DESCRIPTION OF THE INVENTION

This invention relates to the preparation of monoclonal IgM virus/antigen type-common and type-specific HSV antibodies and the detecton of HSV antigens or anti-HSV IgM immunoglobulin in biological fluids by improved immunoassay techniques employing monoclonal IgM HSV virus/antigen specific antibodies and a readably labeled, preferably biotin-avidin based, detection system.

In accordance with one aspect of this invention, hybridoma cell lines are established which synthesize and secrete highly specific IgM monoclonal antibodies to herpes simplex virus antigens. As a first step, animal lymphocytes are immunized according to a specific immunization route and schedule to develop lymphocytes which produce monoclonal antibodies to HSV antigens. These lymphocytes are recovered and are fused with myeloma cells derived from the same animal species to form somatic cell hybrids. The cell hybrids then are propagated in tissue culture or in a syngeneic animal for an indefinite period in order to continuously produce antibody to the HSV antigens.

In the process of this invention, animal lymphocytes are stimulated (immunized) in vivo by a preparation of purified HSV1 or HSV2 antigens. The route and schedule of administration of the purified antigen can be varied. The presently preferred administration mode comprises administrating the antigen in two doses intraperitoneally in complete Freunds adjuvant. Within a few days of fusion the mice are injected with a booster administered in the same manner.

Fusion with myeloma cells is effected with myeloma cells that are sensitive to hypoxanthine-aminopterin-thymidine (HAT) medium by virtue of their lacking enzymes such as thymidine kinase (TK) or hypoxanthine-guanine phosphoribosyl transferase (HGPRT). This allows selection of hybrids to be accompanied by growth in HAT medium. Myeloma cell lines utilized for cell fusions are derived from a BALB/c mouse MOPC 21 myeloma as described by Kohler et al, Eur. J. Immunol., Vol. 6, pp. 292–295 (1976). The myeloma cell line is identified as P3-NS-1/-Ag4-1. Such cells are resistant to 20 ug/ml of 8-azaguanine and die in medium containing hypoxanthine-aminopterinthymidine (HAT). The myeloma cells are grown in a suitable cell growth medium which can be supplemented with glucose, glutamine, and fetal calf serum and optionally penicillin and streptomycin. Other mouse lines can also be utilized for the fusions. Fusion is effected by adding a suspension of the lymphocyte cells to the myeloma cells in the growth medium and centrifuging to form a pellet. The cells are then incubated in a growth medium containing the fusing agent, e.g. polyethylene glycol. Suitable techniques for effecting fusion are described for example in Kohler et al, Eur. J. Immunol., Vol. 6, pp. 511–516 (1976) or Gefter et al, Somatic Cell Genet., Vol. 3, 231–236 (1977). Kennett in "Monoclonal Antibodies" Hybridomas: A new dimension in biological analysis, Kennett et al, eds. Plenum, N.Y., pp. 365–375 (1980).

Hybridomas which synthesize and secrete HSV antibodies directed toward viral antigens then are cultured to establish continuously proliferating cell lines with relatively stable genetic constitutions. The cell lines are cloned to give the progeny of individual cells from each line. The cell lines or clones or propagated indefinitely in tissue culture or in vivo in synegenic hosts where they continue to synthesize and secrete antibody to the HSV antigens. Antibody then is recovered from the tissue culture cells or from ascites fluids or serum of histocompatible host animals by conventional precipitation, ion exchange, delipidation, or affinity chromatography, or the like.

Thus, a preferred process of producing the monoclonal antibodies of the invention comprises immunizing a host animal with a plurality of innoculations of a herpes simplex virus antigen; providing a final antibody stimulating booster inoculation at least about 3 weeks after immunization and prior to lymphocyte cell removal from the host animal; recoverying lymphocyte cells producing antibody from the host animal; forming cell hybrids by fusing said lymphocytes cells to a myeloma cell; selecting anti-herpes simplex specific IgM antibody producing hybrid cells, culturing said hybrids and collecting IgM type-common, type 1 specific, or type 2 specific antibodies against herpes simplex virus. Preferably the host animal is mouse. Also in a preferred embodiment the booster innoculation is performed using antigen in an adjuvant by intraperitoneal administration, with the presently preferred adjuvant being complete Freunds adjuvant.

The hybridomas obtained by the present invention are capable of producing IgM antibody. A deposit of the cell line identified as 1.B.1 is on deposit with the American Type Culture Collection and is assigned ATCC accession number HB 8148. A deposit of the cell line identified as 18.B.2 is on deposit with the American Type Culture Collection and is assigned ATCC accession number HB 8149.

CELL LINES DEPOSITED WITH ATCC

| Characterization myeloma cell line | Fused Cells | |
|---|---|---|
| NS-1 | X | Balb/c Spleen cell immunized with purified HSV2 (strain 186) virions |
| Designation | | |
| M.186.18.B.2 | | ATCC HB 8148 |
| M.186.1.B.1 | | ATCC HB 8149 |
| Secretes | | |
| 18.B.2 | IgM, Kappa Chain | Recognizes HSV1 and HSV2 type-common determinants |
| 1.B.1 | IgM, Kappa Chain | Recognizes HSV2 type-specific determinants |

EXAMPLE 1

The example illustrates that monoclonal antibodies to HSV useful in this invention can be prepared as follows:

Preparation of Immunizing Antigen

African green monkey kidney (Vero) cells, diploid epithelial human lung (MRC-5), and human epitheliod carcinoma (HeP-2) cells were propagated as monolayer cultures using Dulbecco's minimal essential medium (DMEM) supplemented with 10% fetal calf serum (FCS). NS-1 myeloma cells and hybrid cells, generated as described subsequently, were grown in DMEM with 20% FCS. The procedures used for preparing and titrating virus stocks of HSV1 (strain KOS) and HSV2 (strain M186) have been described elsewhere; Courtney et al, *Virology*, 52: 447–455 (1973).

HSV virions were purified by polyethylene glycol precipitation and sucrose gradient cetrifugation as previously described; Dreesman et al, *Virology*, 50: 528–534 (1972). VP 119 glycoprotein was purified from HSV2 infected HeP-2 cells according to the methods described in detail by Courtney et al, Virol. 62: 539–551 (1974).

I. MAINTENANCE OF MYELOMA CELL LINES

Reagents 1. 8-azaguanine or 6 thioguanine resistant mouse myeloma cells. The cell line used was the $P_3$-NS-1/Ag4-1, originally derived from the BALB/c tumor, MOPC 21. This cell line secretes only kappa light chains.
2. Dulbecco's Minimal Essential Medium (DMEM) from Gibco. 4.5 g/l glucose 0.2M glutamine enriched.
3. 7.5% $NaHCO_3$
4. Fetal Calf Serum (FCS). The lot must be selected for nontoxicity to myeloma cells.
5. Sodium pyruvate from Sigma
6. 8 azaguanine (8-AG) from Sigma
7. 6 thioguanine (6-TG) from Sigma
8. 75 $cm^2$, 150 $cm^2$ tissue culture flasks
9. Hemocytometer and 0.2% Trypan Blue

Preparation of Solutions

All solutions must be prepared aseptically and sterility tested.

| Hybridoma Growth Medium | 100 Na Pyruvate | 100 × 8 AG |
|---|---|---|
| 400 ml DMEM pH 7.2<br>60 ml FCS<br>25 ml $NaHCO_3$ | 5 mg/ml $H_2O$<br>4 ml Na pyruvate | 2 mg/ml $H_2O$<br>Adjust to pH 7,2 with NaOH until crystals dissolve. |

100 × 6-TG 250 ug/ml $H_2O$ Adjust pH with 0.1 N NaOH until crystals dissolve.

Note:
Due to the gradual accumulation of hypoxanthineguanine phosphoribosyl transferase (HGPRT) positive cells, the myeloma cells should be treated periodically (3×/year) with 8-AG and/or 6-TG. Simply add the 8-AG or 6-TG solution to the growth medium and grow the cells in the presence of these metabolic poisons. The cells should not be used for fusion for 5-6 passages after treatment due to the possible presence residual levels of these drugs.

Procedure

The myeloma cells must be maintained between $2$–$3 \times 10^5$ and $1 \times 10^6$ cells/ml to ensure logarithmic growth. Usually cells are split 1:3 every other day, but cell counts must be performed weekly to maintain the density between the prescribed limits. The cells require 37° C., 95% humidity, and 5–7% $CO_2$.

Reference

Kruses, P. F., Patterson, M. K. *Tissue Culture Methods and Applications.* Academic Press, N.Y., 1977, p. 475–479.

II. IMMUNIZATION OF ANIMALS

Reagents

1. Complete Freund's Adjuvant (CFA) from Difco
2. Purified antigen
3. Sterile 0.9% saline
4. 2–5 cc luer-lok glass syringes with 20 gauge needles from Hamilton.
5. 10–15 week old female BALB/c mice

Procedure

1. Dilute antigen to 0.5 mg—1.0 mg/ml with the sterile saline.
2. Prepare antigen-adjuvant emulsion by mixing equal volumes of antigen and CFA in the glass syringes.
3. Inject 0.1 ml of emulsion per mouse (25–50 ug) by the intraperitoneal (IP) route.
4. 3 weeks later, repeat step 2.
5. 2–3 days before the cell fusion, inject mouse with 10 ug of antigen in 0.1 ml in CFA IP.

Note: Blood samples can be taken after the second boost to test for specific antibody.

Reference

Benner, R., F. Meima, et al. Antibody Formation in Mouse Bone Marrow. Immunology 27:747, 1974.

III. CELL FUSION

Reagents

1. Antigen sensitized BalB/c mouse
2. Polyethylene glycol 1000 from J. T. Baker
3. DMEM
4. 7.5% $NaHCO_3$ 5. Sodium pyruvate from Sigma
6. Oxaloacetate OAA from Sigma
7. Insulin from Sigma
8. Transferrin from Sigma
9. Glutathione from Sigma
10. 2-Mercaptoethanol from BioRad
11. Hypoxanthine, Aminopterin, Thymidine (HAT)
13. Hepes from Research Organics Inc.
14. (Dimethyl Sulfoxide) from Fisher
15. 96 well cluster dishes from Costar
16. Ficoll-Hypaque
17. 1 sterile garlic press
18. Fetal Calf Serum (FCS)

| 100X OPIT | 100X HAT | 100X Hepes |
|---|---|---|
| 1.5 Oxaloacetate 500 mg Pyruvate 80 mg (2000µ) Insulin 8.0 mg (2000µ) transferin | 13.6 mg Hypoxanthine 72.7 mg Thymidine 40.0 mg Aminopterin | 47.6 g Hepes pH to 7.4–7.6 |
| adjust (q.s.) to 100 ml within H$_2$O adjust pH to 7.5 to dissolve sterile filter | q.s. to 100 ml H$_2$O sterile filter | q.s. to 100 ml sterile filter |

| 100X HT | 100X 2 MEG | Hybridoma Medium |
|---|---|---|
| 13.6 mg Hypoxanthine 72.7 mg Thymidine | 100 ul of 100% 2-mercoptocthanol 10 mg Glutathione | 400 ml DMEM 100 ml FCS |
| q.s. to 100 ml | q.s. to 100 ml | 5 ml OPIT 5 ml 2 MEG 25 ml 7.5% NaHCO$_3$ |
| sterile filter | sterile filter | |

| DMEM-DMSO | 40% PEG |
|---|---|
| 9 ml DMEM 1 ml DMSO | 1 g PEG 1000 1.5 ml DMEM-DMSO |
| sterile filter | |

Note: Supplement the Hybridoma Medium with 5 ml of 100X HAT after the cell fusion. After 2 weeks in HAT, supplement the medium with 100X HT for 2 weeks to dilute any residual aminopterin.

| DMEM-HEPES |
|---|
| 100 ml DMEM |
| 1 ml DMEM |
| 5 ml FCS |

CELL FUSION PROCEDURE

1. Preparation of Mouse

The immunized mouse is anesthesized and exsanguinated by removing the eye. The blood is collected in a siliconized tube to test for antibody. After collecting all the blood that can be recovered, separate the cervical vertebrae by grasping the tail and head firmly and pulling quickly. Immerse the mouse in a 20% Betadine solution for 5 minutes.

2. Preparation of Spleen Cells

Remove the spleen aseptically under the hood and place the spleen in a 60 mm petri dish containing 10 ml of DMEM-Hepes. Wash the spleen and place it in a sterile garlic press. Gently squeeze the press to force individual spleen cells through into a new 60 mm petri dish with 10 ml of fresh DMEM-Hepes. Continue the process until only the white splenic capsule remains in the garlic press. Transfer the cells into a conical centrifuge tube and allow the large pieces of tissue to settle. Transfer the cells to another tube and centrifuge at 1000 rpm for 5 minutes. Remove supernatant and resuspend the pellet in 2 ml of DMEM-Hepes. Gently add the cell suspension on top of 5 ml of Ficoll-Hypaque. Centrifuge at 2000 rpm for 5 minutes to separate the red blood cells from the lymphocytes. Carefully remove the cells that are concentrated at the Ficoll-DMEM interface. Wash the cells 3× with DMEM without FCS. Approximately $1-2 \times 10^8$ cells per spleen.

3. Preparation of Myeloma Cells

Concentrate $1-2 \times 10^7$ mid-log phase myeloma cells (90% or greater viability by trypan blue exclusion) by centrifugation. Wash 3× with DMEM without FCS. Add washed myeloma cells to washed spleen cells.

4. Cell Fusion Procedure

Centrifuge the spleen/myeloma cell mixture. Remove supernatant and gently tap the pellet. Add 0.2 ml of 40% PEG. Mix well but do not pipette vigorously. Start timing the fusion as soon as the PEG is added. The PEG should remain in contact with the cells for a total of 8 minutes. Spin the cells at 1500 rpm for exactly 3 minutes. Leave the PEG on the cells until the 8 minute time period is completed. Remove the PEG at the proper time and tap the cell pellet to loosen the cells. Add 50 ml of DMEM without serum and centrifuge at 1000 rpm. Remove supernatant, loosen the cell pellet, and add 50 ml of hybridoma medium with HAT. Distribute 0.1 ml per well into 96 well cluster dishes. Place the cells in incubator.

Reference: Galfre et al, Nature 266:550, 1977.

IV. SELECTION OF SPECIFIC ANTIBODY PRODUCING CULTURES

Reagents and Procedures

See protocol for detection of specific mouse antibody.

Note: After the cell fusion, the HAT medium will kill most of the cells that are seeded in the 96 well cluster dishes. If the parent myeloma cells are properly treated with 8 azaquanine before the fusion, the only cells that will grow after the fusion will be hybridomas. The hybridomas require 10–14 days before reaching the proper density for screening. Several media changes with fresh HAT medium during the interim between fusion and screening are necessary as indicated by color change due to acid condition of cell growth. When the cells are ready for screening, remove 100 ul from each culture for testing (50 ul×2) by solid phase RIA or ELISA. After identifying the cultures producing specific antibody, transfer the cells to 24 well cluster dishes for expansion and, at the same time, remove an aliquote for cloning. Freeze the cells from the 24 well cluster dishes after the cultures have grown to sufficient numbers ($1 \times 10^7$).

V. CLONING

Reagents

1. SeaKem agarose (from FMC) gels at 36° C. melts at 90° C.
2. SeaPlaque agarose (from FMC) gels at 25° C. melts at 60° C.
3. Mitomycin C from Sigma
4. 3T3 cells (Balb/c fibroblast line)
5. 24 cluster dishes from Costar 6. Hanks balanced salt solution (HBSS) (Gibco)
7. Trypsin-EDTA
8. Millipore filters (0.22 micron)

Preparation of Solutions

| 4 × Seakem | 6 × SeaPlaque |
| --- | --- |
| 2.4 g dry SeaKem agarose<br>0.85 g NaCl<br>q.s. to 100 ml dH$_1$O<br>autoclave, reconstitute<br>to 100 ml dH$_2$O | 2.4 g dry SeaPlaque agarose<br>0.85 g NaCl<br>q.s. to 100 ml dH$_2$O<br>autoclave, reconstitute<br>to 100 ml with dH$_2$O |
| 3T3 Medium | Mitomycin C |
| 400 ml DMEM<br>60 ml FCS<br>25 ml 7.5% NaHCO$_3$ | 100 ml 3T3 Medium<br>2.5 mg Mitomycin C<br>sterile filter |

PROCEDURE

1. Preparation of Feeder Layer

After the 3T3 fibroblast cells are confluent, replace the growth medium with medium containing mitomycin C (25 ug/ml) for 4 hours. Remove mitomycin and wash cells 3× with 20 ml HBSS. Add 10 ml of trypsin-EDTA solution. Centrifuge cells and resuspend in 48 ml of 3T3 medium. Add 0.5 ml of the cell suspension per well to four 24 cluster dishes. Allow the viable cells to attach to the dish for 2 hours. Remove the medium and add 0.5 ml of 0.6% SeaKem agarose diluted from the 4× stock with Hybridoma growth medium (12 ml 2.4% Seakem + 36 ml medium). Incubate the cells at 37° C. overnight.

2. Soft Agar Cloning

After the feeder layer has been prepared, dilute the positive hybridoma cultures to 100 cells/ml with 0.4% SeaPlaque agarose (8 ml of 2.4% SeaPlaque + 40 ml medium), add 0.5 ml of the cell suspension to the 24 well cluster dishes with the feeder layer. Clone 2 hybridoma cultures per plate (6 ml per culture).

3. Picking Clones

10–12 days after cloning, macroscopic clones of cells can be seen in the soft agar layer. Remove individual clones with a sterile 9 inch pasteur pipette. Transfer each clone to individual wells in a 96 well cluster dish. When the cells have filled 75% of the well, test the supernatants for specific antibody. Expand the positive wells. Freeze cells in 1×10$^7$ cells/ml aliquotes.

REFERENCES

Coffino, P., Baumal, R., et al. *Cloning of Mouse Myeloma Cells and Detection of Variants.* Cell Physiol 79:429–440. Yamomoto, N., Ninuma Y. *Clonal Transformation of Human Leukocytes by Epstein-Barr Virus in Soft Agar.* Int. J. Cancer 17 (1976) 191–196.

VI. IN VIVO PROPAGATION

Reagents

Cloned hybridoma cell lines
10 g Balb/c female mice
Pristain (Source)

Procedure

Inject 0.5 ml of Pristain I.P. per mouse 1–2 weeks before injecting 1–2×10$^7$ hybridoma cells in 0.5 ml sterile normal saline. 2–3 weeks later, drain ascites fluid. Centrifuge the cells at 1000 rpm at room temperature. Remove the supernatant and purify the antibody from the fluid. Resuspend the cell pellet in 0.5 ml of sterile normal saline and inject the cells I.P. into another Pristain treated mouse.

VII. FREEZING AND THAWING CELLS

Reagents

Fetal Calf Serum (FCS)
DMSO
Freezing ampoules from NUNC (Southland Cryogenics)
Styrofoam racks −70° C. Revco
Liquid N$_2$ freezer Procedure for Freezing 1. Centrifuge 1×10$^7$ cells in mid-logrithmic growth, i.e., greater than 90% viable.
2. Resuspend the cells in 1 ml of 90% FCS/10% DMSO.
3. Place the ampoules in the styrofoam rack and immediately place the cells at −70° C.
4. 24 hours later, transfer the cells from −70° C. to liquid N$_2$.

Procedure for Thawing

1. Transfer the ampoule from liquid N$_2$ to 37° C. water bath immediately. Centrifuge at 1000 rpm. Resuspend the cells in 10 ml of Hybridoma growth medium.

The antibody containing ascites fluid was diluted to 4% with 5% heparin and delipidated with MnCl$_2$ at a final concentration of 0.25M at 4° C., and subsequently fractionated with 18% (weight/volume) sodium sulfate. The IgM antibodies were then separated by successive gel filtration on Sephacryl S-300 and Sephadex G-200, respectively. The concentration of monoclonal IgM was determined at O.D.$_{280}$ using an extinction coefficient for the 1% solution of 14.

CHARACTERIZATION OF MONOCLONAL ANTIBODY

Radioimmunoassays

A solid phase radioimmunoassay (RIA) was used to screen hybridomas for antibodies to HSV and to characterize the antigenic determinants detected by the monoclonal antibodies. Briefly, infected cell lysates of HSV1, HSV2 and CMV grown in MRC-5 cells or purified HSV1 and HSV2 virions were coated to the wells of flat bottom microtiter plates (Dynatech, Alexandra, Va.) 8 hours at 4° C. The unabsorbed virus was removed and non-specific sites on the wells were blocked with a solution of 1% gelatin in P.B.S. Fifty microliters of either hybridoma supernatant fluid or dilutions of purified IgM monoclonal antibody was added and allowed to incubate for 1 hour at 25° C. Following removal of unbound antibody, the microtiter plates were washed three times with PBS and approximately 50,000 cpm of $^{125}$I-labeled IgG fraction of goat anti-mouse immunoglobulin (GAM) (Cappel Laboratories, Cochranville, Pa.) in 1% gelatin was added. After 1 hour at 25° C., the excess radioactivity was removed and the plates were washed three times with PBS. The wells were cut out and counted in an automatic gamma counter. Each preparation of HSV was titrated to determine the optimal antigen concentration using the prefusion mouse anti-HSV2 serum.

A solid phase RIA was also used to classify the monoclonal antibodies with regard to heavy and light chain isotype. In this assay, 50 ul containing 200 ng of purified monoclonal antibody was coated on the wells of flat bottom microtiter plates for 8 hours at 4° C. Similarly, the wells were blocked with 1% gelatin and dilutions of different rabbit anti-heavy chain and light chain specific antisera (Litton Bionetics Inc., Kensington, Md.) were added.

After 1 hour incubation at 25° C., the plate was washed three times and 50 ul containing 50,000 cpm of $^{125}I$ labeled goat anti-rabbit-globulin (GARGG) (AMF Inc., Seguin, Tex.) was added. The GARGG had been previously adsorbed with mouse globulin to remove heterophile antibody.

Following a 1 hour incubation at 25° C., the excess radioactivity was removed and the wells counted as previously described.

Virus Neutralization

The ability of the IgM monoclonal antibodies to neutralize virus infectivity was determined by a plaque reduction test. Briefly, HSV1 and HSV2 were grown in Vero cells and titrated to give between 50-200 plaques per 0.1 ml of virus. Three hundred microliters containing 300 ug of purified monoclonal antibody was mixed with 300 ul of the virus suspension and incubated for 1 hour at 4° C. Two hundred microliters of the virus antibody suspension were inoculated onto Vero cell monolayers and incubated for 2 hours at 37° C. The addition of medium containing methyl cellulose, fixing and staining of cells after three days, and the counting of plaques were done as previously described (Showalter et al, *Infect. Immun.*, 34:684-692.

Immunofluorescence (IF)

The procedure for IF was according to that of Showalter et al, supra. Vero cells were infected with HSV1 and HSV2. Twenty micrograms of the purified IgM monoclonal antibody was added to acetone-fixed cells and indirect immunofluorescence obtained with fluorescein isothiocynate conjugated GAM (Cappel Laboratories). Infected cell surfaces were examined similarly, but the cells were not fixed.

Analytical Isoelectricfocusing

Isolectric focusing (IEF) of IgM monoclonal antibodies was performed in 5% polyacrylamide gels as previously described (O'Farrell, *J. Biol. Chem.*, 250:4007-4021). The isoelectric points ($P_I$) of the antibodies were determined from a standard curve (IEF calibration kit; Pharmacia) based on the distance migrated from the anode.

Iodination

Fifty micrograms of IgG fractions of GARGG and GAM were labeled with $Na^{125}I$ (Amersham Corp.) using Enzymobeads (BioRad Laboratories, Richmond, Calif.). Free $Na^{125}I$ was separated from $^{125}I$ labeled protein on PD-10 columns (Pharmacia). The percent $^{125}I$ label precipitated by 10% trichloroacetic acid was greater than 95%.

RESULTS

1. HSV specificity of monoclonals by RIA

Figure 5:
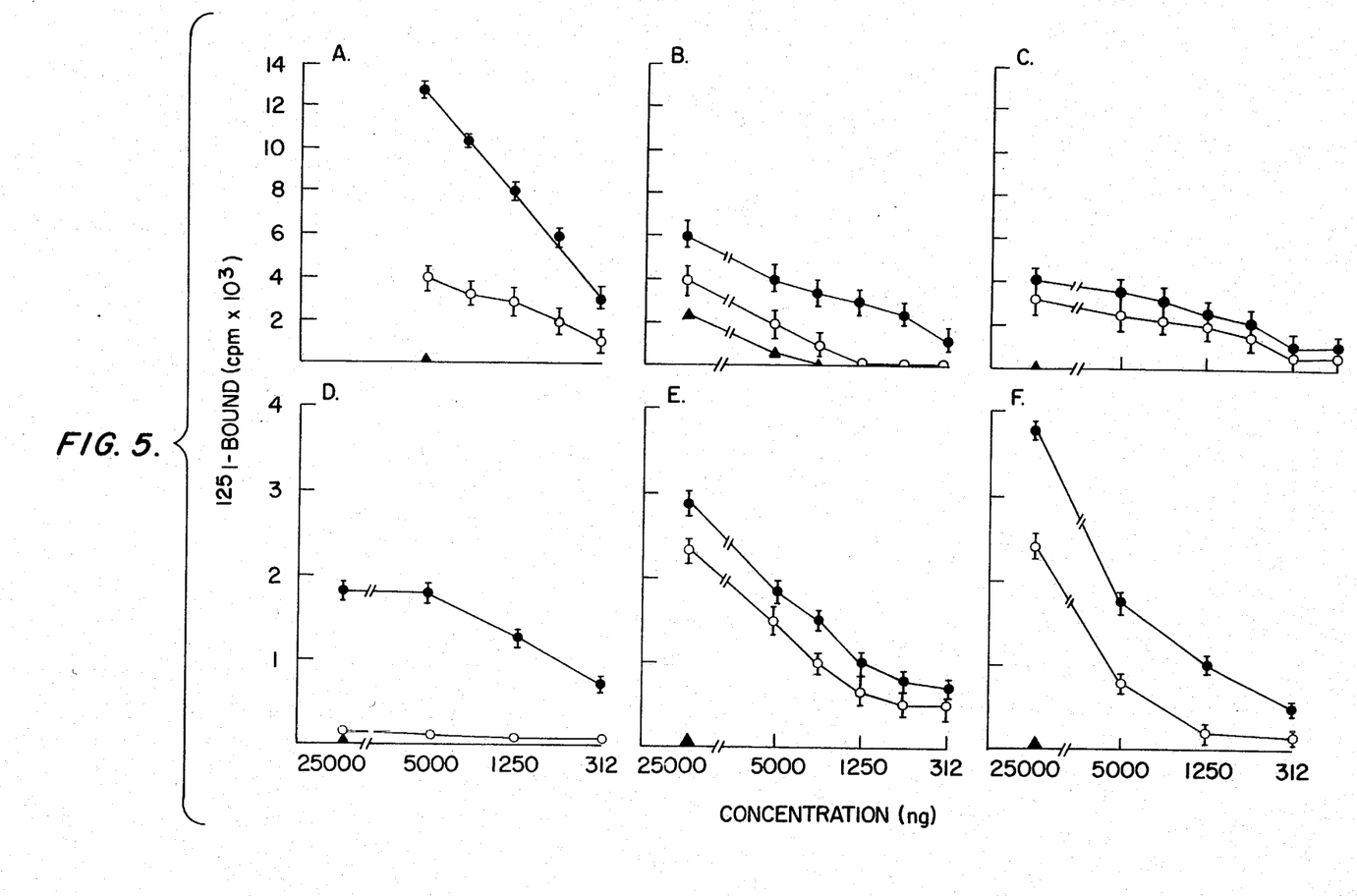
FIG. 5 is a binding analysis of six monoclonal antibody preparations by RIA for activity to HSV1, HSV2, and to uninfected cell lysates (Example 1) which are represented by O, ●, and ▲, respectively. Brackets refer to the range of triplicate values. The monoclonal antibodies are shown in Panel A, 18.B.2; Panel B, 12.A.3; Panel C, 2.A.2; Panel D, 1.B.1; Panel E, 7.B.2; and Panel F, HS.2.A.

The binding analysis of six monoclonal antibodies to HSV1, HSV2 and mock infected MRC-5 cell lysates is shown in FIG. 5. Monoclonal antibodies 2.A.2 (FIG. 5C), 7B (FIG. 5E), and HS.2.A (FIG. 5F) recognized type-common antigenic determinants shared by both HSV1 and HSV2. Since the slopes of their respective binding curves did not differ significantly, these antibodies apparently detected a similar determinant present on HSV1 and HSV2. The inability of these three antibodies to bind a mock cell lysate ruled out the possibility that the antigenic determinant was found in MRC-5 host cell material. Antibody 12.A.3 (FIG. 5B) also detected HSV type-common antigenic determinants; however, since binding was also demonstrated to the mock cell lysate, this monoclonal antibody recognizes either MRC-5 derived host material or a determinant shared by virus and host cells. Antibody 18.B.2 showed more efficient binding to HSV2 than HSV1 (FIG. 5A). In this regard, at a concentration of 5 ug, 12,800 cpm and 4000 cpm were bound with HSV2 and HSV1 antigens, respectively. Although 18.B.2 detects a type-common antigen on HSV1 and HSV2 while failing to bind the mock cell lysate, it appears to react preferentially with HSV2.

Antibody 1.B.1 apparently recognized a HSV2 type-specific antigenic determinant (FIG. 1D). This was indicated by the inability of 1.B.1 to bind either HSV1 or mock infected cell lysates; whereas, a significant degree of binding was demonstrated to HSV2. It is of further interest to note that antibodies 1.B.1, 2.A.2, 18.B.2 and HS.2.A failed to bind purified CMV or a representative number of enterviruses in an RIA, while 7.B.2 demonstrated minor reactivity and 12.A.3 bound CMV similar to that seen with mock infected cells (data not shown).

2. Neutralization

The ability of the monoclonal antibodies to neutralize HSV infectivity was based on plaque reduction and is shown in Table 1. At concentrations of either 300 ug or 30 ug, IgM antibodies 18.B.2, 12.A.3 and 7.B.2 failed to significantly neutralize either HSV1 or HSV2 infectivity. Both antibody 2.A.2 and 1.B.1 were capable of partially neutralizing HSV. Attesting further to the type-common specificity of 2.A.2 was a reduction in the numbers of HSV1 and HSV2 plaques by 42% and 50%, respectively. When the concentration of 2.A.2 was reduced from 300 ug to 30 ug, a decrease in plaque reduction was noted with the two types of virus. The type-specific nature of antibody 1.B.1 was further demonstrated by the partial neutralization (60%) of only HSV2 infectivity. No reduction in the number of plaques by 1.B.1 was seen in HSV1 infected Vero cells.

Since two of the monoclonal antibodies were inefficient in neutralizing viral infectivity, requiring large amounts of antibody (300 ug) for partial plaque reduction, different combinations of antibodies were tested for their combined effect on neutralizing HSV2 infectivity. It was thought that antibodies which failed to completely abolish infectivity in the neutralization test may react with only a portion of the antigenic determinant(s) necessary to prevent viral infectivity. Addition of several monoclonal antibodies might generate an enhancing or additive effect with respect to neutralization activity. However, various combinations of the monoclonal antibodies (except for HS.2.A) were no more efficient at neutralizing HSV2 infectivity than the individual antibodies alone (data not shown).

The only monoclonal that completely abolished HSV infectivity was HS.2.A. After a concentration of 30 ug, HS.2.A reduced HSV1 and HSV2 PFU by 100%. A concentration of 500 ng reduced PFU in HSV2 infectivity by 50%. Although the concentration of HS-2.A that reduced HSV1 PFU by 50% was not determined, the type-common nature of antigenic determinants recognized by HS.2.A was suggested by the neutralization test.

3. Characterization of Ig Isotype and $P_I$

Using a solid phase RIA with rabbit anti-heavy and light chain specific antisera, all six monoclonal antibodies were found to be of the IgM heavy chain class with kappa light chains (Table 2). Attesting further to the Ig class specificity was the finding that all of the antibodies were detected in the void volume of Sephadex G-200 and reduction followed by SDS-polyacrylamide gel electrophosesis (PAGE) generated heavy chains with an approximate molecular weight of 70,000 daltons. It is of interest to note that two light chains were detected by SDS-PAGE with antibody 12.A.3. One of these light chains appeared to be of NS-1 origin, whereas the other was probably from the spleen cell parent.

Analytical IEF on 5% polyacrylamide gels of the purified IgM monoclonal antibodies indicated a narrow range of $P_I$ (Table 2). This range was from 7.7 to 8.25 for HS.2.A and 1.B.1, respectively. This data corresponds well to the $P_I$ determined by preparative IEF in sucrose, where anti-HSV activity was also assayed. In this regard, the $P_I$ determined by preparative IEF for antibodies 2.A.2, 1.B.1 and 18.B.2 were 8.0, 8.1 and 8.3, respectively, which are similar to the values obtained by analytical IEF.

4. Immunofluorescence

The indirect immunofluorescence of the monoclonal antibodies with acetone fixed HSV1 and HSV2 infected Vero cells was measured. As predicted by the RIA and neutralization tests, antibodies 2.A.2 and 1.B.1 recognized type-common and type-specific HSV determinants, respectively. Antibody 1.B.1 demonstrated a nuclear pattern of immunofluorescence with HSV2 infected cells while no fluorescence was detected with HSV1 infected cells. Nuclear immunofluorescence was also demonstrated by antibody 2.A.2 with both HSV2 and HSV1 infected cells. The intensity of fluorescence generated by antibodies 2.A.2 and 1.B.1 was similar to that produced by a polyclonal mouse anti-HSV2 antiserum.

Reaffirming the type-common antigenic determinants detected by antibody 7.B.2 in the RIA was the cytoplasmic patterns of immunofluorescence produced in HSV2 and HSV1 infected cells. No immunofluorescence staining was detected with antibodies 18.B.2 and 12.A.3 using acetone fixed cells, whereas HS.2.A produced a weak cytoplasmic staining with HSV2 infected cells only.

It was a paradox that antibody 18.B.2, which demonstrated the most efficient binding to HSV in RIA, failed to either neutralize viral infectivity or stain virus infected cells. To determine if antibody 18.B.2 would demonstrate surface staining of virus infected cells, indirect IF was performed on unfixed HSV-infected cells. There was surface staining of both HSV1 and HSV2 infected cells, whereas no staining was observed with mock infected cells.

TABLE 1

VIRUS NEUTRALIZATION-PLAQUE REDUCTION ASSAY

| Antibody | Concentration | % PFU reduction HSV-1 infected Vero cells | % PFU reduction HSV-2 infected Vero cells |
|---|---|---|---|
| M.186.2A.2 | 300 μg | 42 | 50 |
| | 30 μg | 28[a] | 37 |
| M.186.18B.2 | 300 μg | 5 | 7 |
| | 30 μg | 0 | 2 |
| M.186.1B.1 | 300 μg | 0 | 64 |
| | 30 μg | 0 | 56 |
| M.186.7.B.2 | 300 μg | 6 | 8 |
| | 30 μg | 0 | 4 |
| M.186.12.A.3 | 300 μg | 0 | 4 |
| | 30 μg | 0 | 0 |
| Mouse anti-HSV-2 | | 100 | 100 |
| Normal Mouse Serum | | 4 | 0 |
| HS.2.A. | 30 μg | 100 | 100[b] |

[a]Mean of duplicate experiments
[b]A final concentration of 500 ng reduced by PFU by 50%.

TABLE 2

CALSSIFICATION OF MONOCLONAL ANTIBODIES

| Ab Designation | Immunizing Antigen | Heavy & Light chain Composition[a] | $P_I$[b] |
|---|---|---|---|
| M.186.1B.1 | HSV-2 | μ, κ | 8.25 |
| M.186.2A.2 | HSV-2 | μ, κ | 7.95 |
| M.186.7B.2 | HSV-2 | μ, κ | 7.9 |
| M.186.12.A.3 | HSV-2 | μ, κ | 8.05 |
| M.186.18.B.2 | HSV-2 | μ, κ | 8.1 |
| HS.2.A. | VP119 | μ, κ | 7.7 |

[a]H & L chain composition was determined by SDS-PAGE and a solid phase R.I.A. employing isotype-specific antisera
[b]Isoelectric points were determined in 5% polyacrylamide gels.

TABLE 3

| | Immunofluorescence | | R.I.A. binding to | | Neutralization | | |
|---|---|---|---|---|---|---|---|
| Ab | HSV-1 | HSV-2 | HSV-1 | HSV-2 | HSV-1 | HSV-2 | Reactivity |
| M.186.1.B.1 | — | nuclear | — | + | — | + | type-specific |
| M.186.2.A.2 | nuclear | nuclear | + | + | + | + | type-common |
| M.186.7.B.2 | cyto | cyto | + | + | — | — | type-common |
| M.186.12.A.3 | — | — | + | + | — | — | type common |
| M.186.18.B.2 | +[a] | +[a] | + | + | — | — | type-common |
| HS.2.A | — | +/— | + | + | + | + | type-common |

[a]Surface I.F. was seen when the cells were not fixed with acetone.

Preparation of monoclonal IgM anti-HSV antibody and biotin labeling

The IgM antibody was labeled with biotin by the following method: A one milliliter volume of IgM at a concentration of 10 milligrams per milliliter was dialyzed against a 0.1 molar sodium bicarbonate overnight at 4° C. A solution of 3.4 milligrams of biotinyl-N-hydroxysuccinimide (BNHS) (Cal Biochem) per 100 microliters of dimethylformamide was prepared. 285 microliters of the BNHS solution was added to the 1 milliliter volume of IgM (10 milligrams per milliliter) and incubated at room temperature for one hour, with occasional mixing. The resultant solution was then dialyzed for 24 hours again at 4° C. against several changes of phosphate buffered saline (pH 7.2) (PBS). After dialysis, the antibody solution was mixed with an equal volume of double distilled glycerol and stored at minus 20° C.

Preparation of monoclonal IgM anti-HSV2 antibody and biotin labeling

Spleen cells from mice immunized with purified HSV2 virions were fused with NS-1 myeloma cells as described previously hereinabove. Both HSV1 and HSV2 were used to screen for antibodies. Those cells positive for anti-HSV2 only were used to generate ascites tumors. The resultant monoclonal IgM antibody was isolated and labeled as described hereinabove.

Preparation of monoclonal IgM anti-HSV1 antibody and biotin labeling

The procedure used to prepare these antibodies is the same as described above as for the HSV2 antibodies, except that those cells positive for anti-HSV1 only are used to generate ascite tumors. Purification of the antibody and biotin labeling are conducted as described above.

IMMUNOASSAY PROCEDURES

Figure 1:
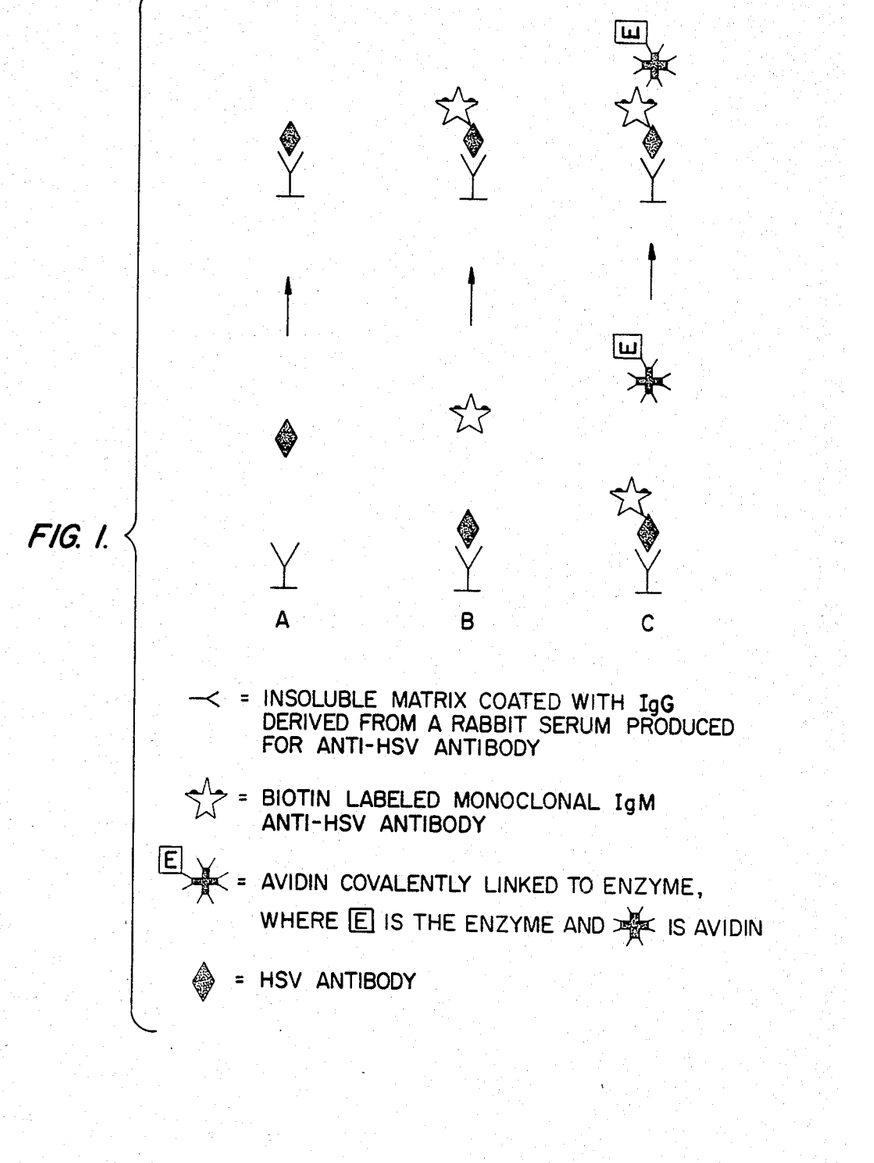
FIG. 1 is a schematic diagram of the basic amplified enzyme-linked immunosorbent assay (ELISA) of the invention, which detects herpes simplex virus antigen.

The preferred methods of the invention relate to the demonstration and determination of herpes simplex viruses (HSV1 and HSV2). With reference to FIG. 1, an insoluble matrix is coated with a polyclonal antibody (prepared in a non-mouse species) against herpes simplex viruses (i.e., an antibody cross-reactive with both HSV1 as well as with HSV2. A biological sample fluid, the HSV antigen content of which is sought to be determined, is incubated with the antibody coated matrix to immunocapture HSV antigen if present (FIG. 1A).

The resultant matrix, separated from the uncaptured sample, is then incubated with a quantity of biotin labeled mouse monoclonal IgM anti-HSV antibody (cross-reactive with both HSV1 and HSV2 or specifically reactive with only one type sufficient to bind a measurable number of HSV antigens; if present (FIG. 1B). The resultant matrix separated from uncaptured monoclonal antibody and the matrix is then incubated with a quantity of labeled avidin, preferably enzyme labeled avidin sufficient to bind a measurable number of labeled monoclonal antibodies if present (FIG. 1C). The resultant matrix is separated from uncaptured avidin and the label detected and/or preferably quantified to thereby determine indirectly the presence of HSV antigen in the sample. Where the label is an enzyme, the matrix is incubated with an enzyme reactive substrate and the change in the substrate, e.g. color change or fluorescence emission detected.

In the above procedure, where the monoclonal antibody is cross-reactive to HSV1 and HSV2, the test can be employed as a general HSV screening test with subsequent determination of the HSV type present by other appropriate means, if desired, including the repeating of the procedure with a monoclonal IgM antibody specific for one of the two HSV types.

In one embodiment of the invention, the basic procedure of FIG. 1 is modified by the use of an added amplification step. In this embodiment, the basic procedure is followed through the incubation of the sample fluid. The sample is then incubated with a sufficient quantity of separated monoclonal IgM antibody (not coupled to biotin) (FIG. 2B). The matrix is then incubated with a quantity of biotin labeled antibody against the monoclonal antibody or a biotin label reactive fragment of such an antibody which reacts with said monoclonal antibody (e.g., biotin labeled Fab') sufficient to bind a measurable number of monoclonal antibodies if present, e.g., goat anti-mouse IgM immunoglobulin (FIG. 2C). The resultant separated matrix is then incubated with an enzyme-avidin conjugate (FIG. 2D), as in the basic procedure (FIG. 1). This procedure yields a significantly greater sensitivity on the basic procedure.

In a further embodiment of the invention (FIG. 3), the sample contacted matrix, formed as above, is incubated with biotinylated monoclonal IgM antibody. The resultant separated matrix is then incubated with native avidin and after subsequent separation is reacted with biotinylated enzyme, each reagent in a sufficient measurable quantity thus amplifying the detectability of the presence of the HSV antigen.

Figure 4:
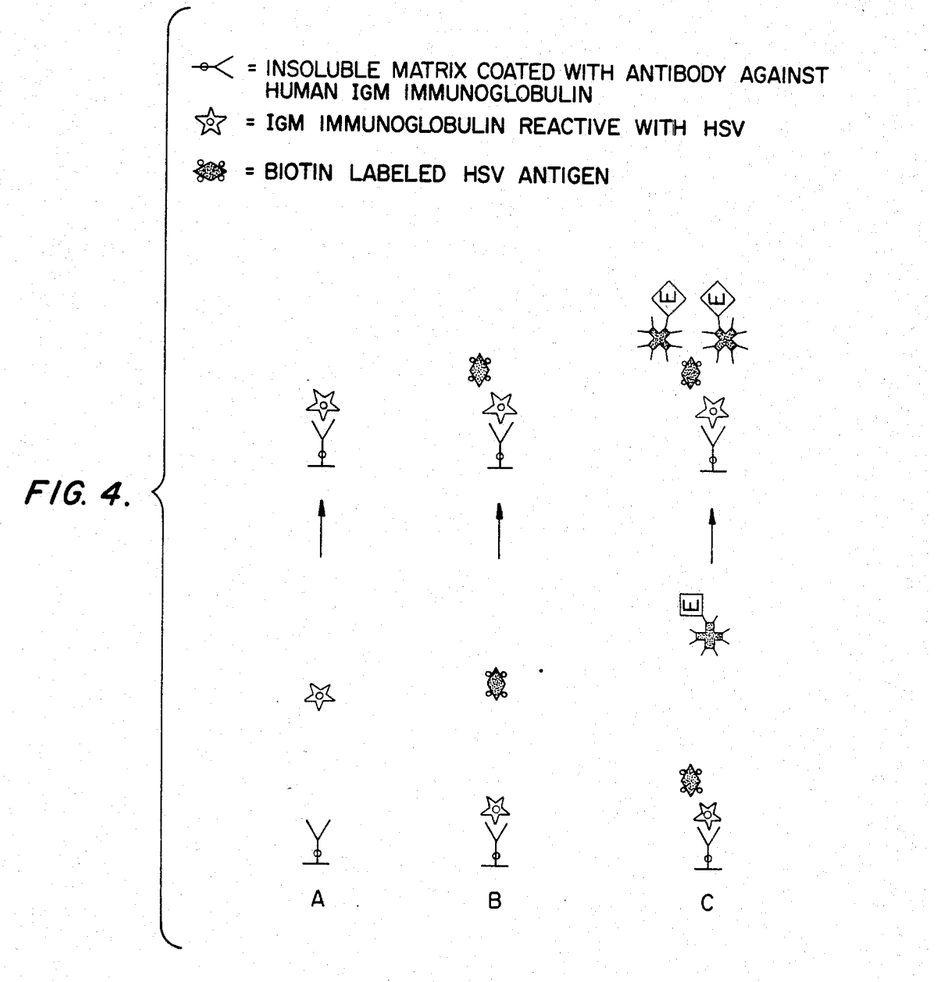
FIG. 4 is a schematic diagram of a test for the detection of HSV and IgM antibody.

A distinct alternative assay for herpes simplex virus infections involves the detection in a biological sample of IgM antibody against HSV. In this method (FIG. 4) an insoluble matrix is coated with a polyclonal antibody specific for the mu-chain of IgM immunoglobulin sought to be determined in a biological sample fluid. The coated matrix is then incubated with a biological fluid sample to immunocapture IgM immunoglobulin, if present (FIG. 4A). The matrix is separated and is then incubated with a quantity of biotin labeled virus sufficient to bind a measurable number of captured IgM molecules specific for HSV, if present. If the sample contained IgM with anti-HSV activity, specific combination will take place. The matrix is separated and is then incubated with avidin-enzyme conjugate, or otherwise labeled avidin as above, which in turn will bind to the biotinylated virus if it was bound.

Instead of an enzyme labeled avidin or biotin, the avidin or biotin conjugate can be labeled with a radioisotope marker such as, for example $125_I$ by known techniques. A further alternative is the labeling of avidin with a fluorescent marker such as, for example, fluorescein, rhodamine, fluorescamine and 8 aneleno-1-naphthalene sulfuric acid, again by techniques generally described in the literature.

The use of enzyme labels in immunoassays is generally known, as are techniques for binding enzymes to avidin or biotin. Enzymes and substrates known in the art are useful herein. The enzymes employed are preferably determinable colormetrically or spectrophotometrically. Useful enzymes generally include catalase, peroxidase, beta-glucoindase, beta-D-glucosidase, beta-D-galactosidase, urease, glucose oxidase, galactose oxidase and alkaline phosphatase; in general, the glucuronidases, galactosidases, ureases and the oxicloredentases. The presently preferred enzymes are alkaline phosphatase and horseradish peroxidase.

Another particularly useful enzyme system is beta-galactosidase employed in conjunction with a fluorogenic substrate, with the reading being made with a fluorometer. The substrate of choice in this system is 4-methyl-umbelleferyl-beta-D-galactopyranoside.

While the preferred embodiment of the invention comprises the use of a biotin-avidin system, in an alternative embodiment the biotin-avidin system may be omitted and the readable label (enzyme, radioactive atom, etc.) attached directly to the IgM monoclonal HSV antibody or to the antibody or antibody reactive fragment specific to HSV IgM antibody.

The insoluble reactive antibody bearing matrix may be formed by any means such as those known in the literature. Thus, antibodies can be made insoluble, for example, by crosslinking, by physical absorption, or chemical coupling to an insoluble carrier, such as cellulose compounds, agarose, crosslinked dextran, polystyrene and the like.

EXAMPLE 2

A basic method of the invention (illustrated in FIG. 1) comprises forming an insoluble matrix comprising non-mouse IgG anti-HSV, which is then contacted with the sample to be analyzed, thereby fixing the anti-HSV antigen present to the matrix. The matrix is then separated from the unbound sample and contacted with a preselected quantity of biotinylated monoclonal antibody against HSV to fix the monoclonal antibody to any HSV antigen present on the matrix. After isolation of the matrix, the matrix is then contacted with a preselected quantity of avidin coupled enzyme, in turn fixing the enzyme to any monoclonal antibody previously fixed to the matrix. The matrix is again separated and the presence and/or amount of the enzyme affixed to the matrix determined, thereby detecting and/or quantifying the amount of HSV antigen present in the sample being analyzed.

Preparation of IgG derived from a rabbit serum positive for anti-HSV antibody Rabbit serum positive for anti-HSV antibody was fractionated by successive additions of 18% and 12% (weight/volume) sodium sulfate. The resulting immunoglobulins were fractionated in columns of DEAE-cellulose or Sephadex G-200 (Pharmacia) by which the IgG is separated from other immunoglobulins. The concentration of the rabbit IgG was determined using an extinction coefficient for a 1% solution of 15.0 at an O.D.$_{280}$.

Preparation of avidin covalently linked to enzyme

Five milligrams of alkaline phosphatase (Sigma No. P5521) was centrifuged and the pellet resuspended in 0.9 milliliters of PBS. The suspension was dialyzed overnight against PBS and the volume brought up to 1.3 milliliters with PBS. The alkaline phosphatase was activated with 65 microliters of 25% gluteraldehyde (a final concentration of 1.25% gluteraldehyde).

The solution was rotated for 18 hours at room temperature and then dialyzed against carbonate-bicarbonate buffer (pH 9.6) for 24 to 48 hours. Avidin (Vector Laboratories No. A2000) was added at a 1:1 molar ratio and the mixture incubated at 4° C. for 24 to 48 hours. The resultant conjugate was dialyzed against 0.05 Molar tris 0.15 Molar saline pH 8 plus sodium azide. The conjugate product was then diluted 1:1 with tris saline azide plus 2% bovine serum albumin (BSA) and stored at minus 20° C.

The optimum dilutions of avidin alkaline phosphatase and biotinylated monoclonal IgM anti-HSV was determined with a checkerboard titration, increasing the dilutions of the biotinylated monoclonal IgM anti-HSV and the avidin alkaline phosphatase against a constant amount of HSV2 antigen.

Detection of herpes simplex antigen in biological sample

The tests were conducted in the following manner: Flat bottom wells of 96 well polystyrene microtiter plates were coated with 200 ng rabbit IgG anti-HSV (50 ul/well), in 0.3M carbonate-bicarbonate buffer (pH9.5), and incubated overnight at 4° C. The wells were postcoated with 0.5% gelatin-PBS (200 ul/well) incubated for 30 minutes at 22° C. The wells were washed once with 0.01% gelatin-PBS (200 ul/well). Samples to be tested were added (50 ul/well) to each of two wells and incubated for 2 hours at 45° C. (water bath). The wells were then washed three times with 0.01% gelatin-PBS (200 ul/well). Biotinylated monoclonal IgM anti-HSV (type common) diluted 1:800 in 0.1% gelatin-PBS was added to the wells (50 ul/well) and incubated for 1 hour at 37° C. (water bath). The wells were then washed three times with 0.01% gelatin-PBS. Avidin-alkaline phosphatase (Vector Laboratories) diluted 1:25 in 0.1% gelatin-PBS was then added to the wells (50 ul/well) and incubated for 20 minutes at 22° C. The wells were washed three times with 0.01% gelatin-PBS/200 ul/well. The wells were incubated with substrate: 0.1% P-Nitrophenyl phosphate in 10% diethanolamine, 0.5 mM MgCl$_2$ (200 ul/well), and absorbancy monitored at 405 nm.

The results were as follows

Clinical specimens were collected from lesions by swabing the vesicles with a dry cotton swab and placed in 2 ml veal infusion broth (VIB) aliquoted in sterile 1 dram vials. Each sample was stored frozen at −70° until testing. Each sample was thawed and tested for virus infectivity by inoculation with 0.2 ml sample/test tubes pre-seeded with Vero cells. The cytopathic effect (CPE) was read microscopically daily for 4 days. Those cell sheets exhibiting a typical HSV CPE were recorded as positive for infectivity. On the same day on which the samples were tested for infectivity, they were tested by the Biotin/avidin enzyme linked immunosorbent assay (BA-ELISA) described above (FIG. 1).

To date, 159 samples have been collected from lesions associated with the lips, cervix, vulva, throat, penis and breast. The results were recorded as follows: 17% (27/159) were positive for both antigen and for infectivity; 36% (58 of 159) were negative by both tests; 29% (46 of 159) were antigen positive as tested by BA-ELISA, but did not contain infectious virus; and 9% (14 of 159) were negative by BA-ELISA but were infectious for tissue culture. The remaining 14 samples were too contaminated to be tested by tissue culture, 9 of which were BA-ELISA positive and 5 were BA-ELISA negative.

The validity of the results obtained for samples that were positive for one test but negative by the second method was tested with a control model study in which rabbit eyes were infected with HSV. Two HSV1 isolates were chosen and 12 rabbits were infected with each virus isolate. Tear duct samples were collected at 3 days, 4 days, and 24 days and tested by BA-ELISA for HSV antigens and by tissue culture for infectivity. On day 3, 8/12 rabbits inoculated with isolate 1 and 9/12 inoculated with isolate 2 were positive for antigen. Tear secretions collected on day 3 from all 24 rabbits contained infectious HSV. By day 4, both antigen and infectious virus were detected in 100% of the rabbits. By day 24, infectious virus was not detected in any of these rabbits. However, 100% of the samples collected on day 24 were antigen positive when tested by BA-ELISA.

In summary, it can be concluded that a small burst of infectious virus may be detected by culture which contains too little antigen to be detected by ELISA. However, in twice as many samples collected from lesions, an active virus infection can be detected by expression of HSV antigens, but little or no infectious virus is present.

EXAMPLE 3

The rabbit IgG anti-HSV is the same as employed in Example 1. The monoclonal antibody employed herein is the same as described in Example 1, except that there is no biotin labeling.

Preparation of biotinylated antibody against monoclonal antibody goat IgG anti-mouse IgM-biotin)

Goat anti-mouse IgM serum was passed through a Sepharose linked rabbit IgG column to absorb any immunoglobulins that bind rabbit IgG from the serum. The serum was fractionated by successive 18% and 14% (weight/volume) sodium sulfate precipitations. The resulting immunoglobulins were subjected to chromatography on Sephadex G-200 to separate the IgG from other immunoglobulins. The resultant IgG was labeled with biotin by dialyzing a one milliliter volume of IgG at a concentration of 10 milligrams per milliliter against 0.1 molar sodium bicarbonate overnight at 4° C. A solution of 3.4 milligrams of biotinyl-N-hydroxy-succinimide (Cal Biochem) per 100 microliters of dimethyl formamide was prepared. 57 microliters of the BNHS solution was added to the 1 milliliter volume of IgG (10 milligrams per milliliter) and the mixture incubated at room temperature for one hour, with occasional mixing. The resultant solution was dialyzed for 24 hours at 4° C. against several changes of PBS. After dialysis, an equal volume of double distilled glycerol was added and the mixture stored at minus 20° C.

Preparation of biotinylated Fab' against IgM Immunoglobulin

Fab' fragments are prepared for IgG preparations derived from goat anti-mouse IgM antiserum. Goat anti-mouse IgM antibody is digested in acetate buffer at pH 3.9 with 2% pepsin for a period of 4 hours as previously described (Cabral, G. A., Gyorkey, F., Gyorkey, P., Melnick, J. L., and Dreesman, G. R. Exptl. Molec. Path. 29: 156–169, 1978). The reaction mixture is neutralized after the 4 hour digestion period by addition of 0.1N NaOH and the protein is precipitated by addition of 25% $Na_2SO_4$, to a final concentration of 18%. The resultant F(ab')$_2$ fragment is reduced with 0.007M dithiothreitol at pH 7.0 for 2 hours at 37° C. Dry iodoacetamide is then added to a final concentration of 0.015M and a protein solution will be incubated for an additional 2 hours at 37° C. The mixture is subsequently fractionated by gel filtration in Sephadex G-100, and the fractions containing protein with a molecular weight of 50,000 daltons are concentrated to 5 mg/ml by Amicon filtration using a PM 10 filter.

The fragments are labeled by biotin in a manner similar to that described directly above.

The enzyme avidin coupling product of Example 2 was employed herein.

Test Procedure

Figure 2:
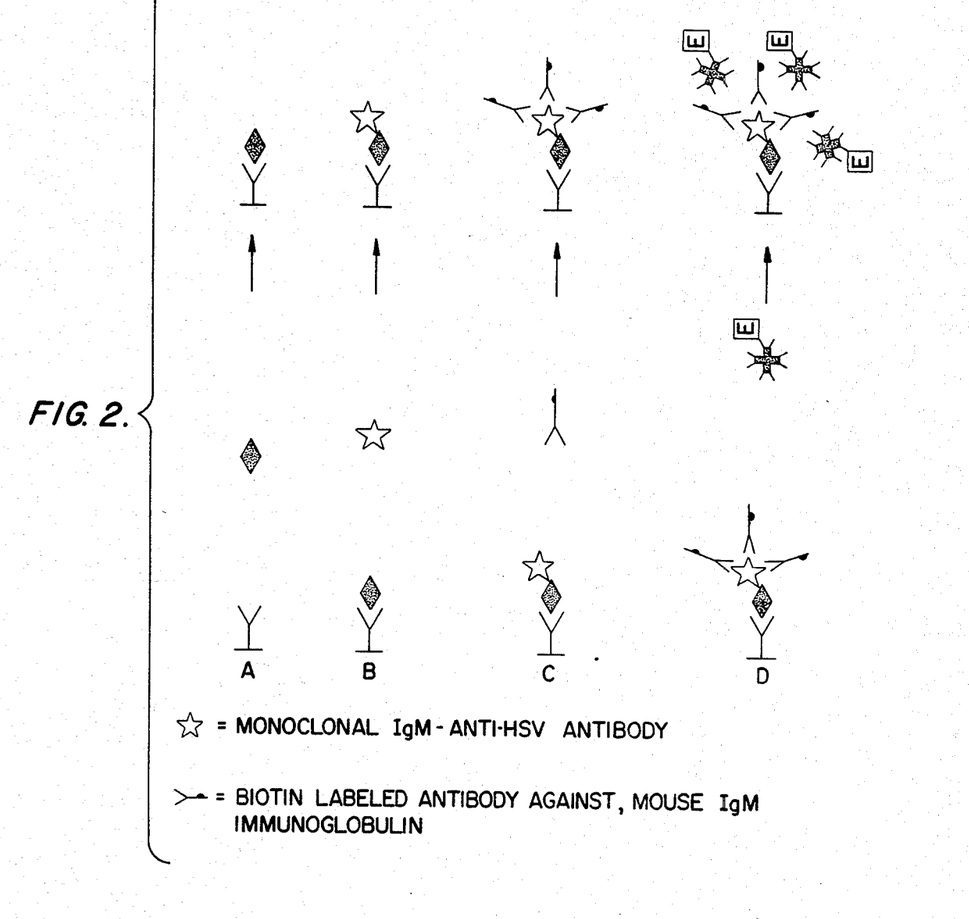
FIG. 2 is a schematic diagram of the basic test containing a second amplification step.

With reference to FIG. 2, the process exemplified herein, an insoluble matrix is formed comprising non-mouse IgG anti-HSV. The matrix is then contacted with samples to be tested, to fix any HSV antigen present to the matrix. The matrix is then separated from the supernatant and in turn contacted with a determination effective amount of monoclonal antibody against HSV. The matrix is then again separated from the supernatant and the matrix is then contacted with an excess of biotin labeled IgG antibody against the IgM monoclonal antibody to fix it to any monoclonal antibody present on the matrix. The matrix is then separated from the supernatant and the matrix is then contacted with tagged avidin to fix the avidin to any biotin previously fixed to the matrix. The tag on the fixed avidin is then measured either quantitatively or qualitatively, to determine the presence and/or amount of HSV antigen which has been fixed to the matrix.

In a manner consistent with the above general method, the following protocol has been developed: flat bottom wells of 96 well polystyrene microtiter plates are coated with 200 nanograms (50 microliters per well) of rabbit IgG anti-HSV, diluted in carbonate-bicarbonate buffer (pH 9.5) and incubated overnight at 4° C. The wells are post-coated with 0.5% gelatin-PBS (200 microliters per well) and incubated for 30 minutes at 22° C. The wells are washed once with 0.01% gelatin-PBS (200 microliters per well). Samples to be tested are added to duplicate wells (50 microliters per well) and incubated for two hours at 45° C. (water bath). The wells are washed three times with 0.01% gelatin-PBS. The above-described monoclonal antibody diluted in 0.1% gelatin-PBS is added to the wells and incubated for one hour at 37° C. (water bath). The wells are then washed three times with 0.01% gelatin-PBS. The biontinylated goat IgG mouse IgM antibody diluted in 0.1% gelatin-PBS is added to the wells and incubated for 1 hour at 37° C. The wells are then washed three times with 0.01% gelatin-PBS. Avidin alkaline phosphatase (Vector Laboratories) diluted 1:25 in 0.1% gelatin-PBS is then added to the wells and incubated 20 minutes at room temperature. The wells are then washed three times with 0.01% gelatin-PBS. Two hundred microliters per well of substrate (as in Example 1) is added to the wells and absorbancy monitored at 405 nm.

The optimal dilution of the two reagents, type-common anti-HSV monoclonal antibody and biotinylated goat anti-mouse IgM reagent was tested in a checkerboard titration testing increasing dilutions of each against a known HSV positive control. For test design (FIG. 2), optimal sensitivity was noted when monoclonal antibody was added at a dilution of 200 nanograms per milliliter and subsequently reacted with a 1:400 dilution of biotin labeled goat anti-mouse IgM reagent.

A challenging application of the BA-ELISA is presented in the possible detection of HSV specified antigens secreted into the spinal fluid obtained from patients with viral encephalititis. The only known diagnostic procedure available is the detection of HSV antigens by fluorescent antibody staining techniques in brain biopsy tissue. In a small preliminary study we have detected HSV antigen by the BA-ELISA technique in spinal fluid from HSV brain biopsy positive patients. The technique illustrated in FIG. 2 was utilized in this study.

EXAMPLE 4

Figure 3:
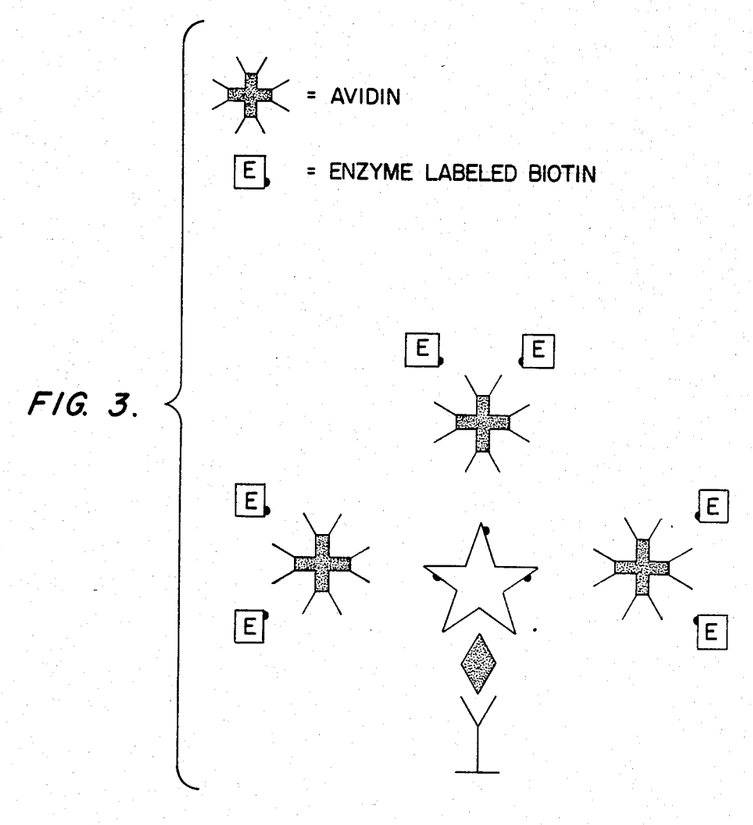
FIG. 3 is a schematic diagram of a modification where native avidin is used to crosslink biotinylated antibody and biotinylated enzyme.

With reference to FIG. 3, the procedure herein exemplified relates to forming a matrix comprising IgG anti-HSV and contacting that matrix with the sample to fix HSV present in the sample to the matrix, and separating the matrix from the supernatant, contacting the resultant matrix with a determination effective amount of biotin labeled monoclonal antibody, separating the supernatant, and contacting the matrix with a determination effective amount of native avidin and separating the supernatant, then contacting the matrix with tagged biotin and reading the tag on the biotin to qualitatively or quantitatively determine the amount of HSV antigen in the sample.

The rabbit IgG anti-HSV antibody employed in this example is the same as prepared in Example 2. The biotinylated monoclonal antibody employed in this example is the same as prepared in Example 1. The native avidin was obtained from Vector Laboratories, Incorporated (Product No. A2000). Biotinylated alkaline phosphatase was obtained from Vector Laboratories, Incorporated (Catalog No. B-2005).

An example of the general procedure outlined above is as follows: flat bottom wells of a 96 well polystyrene microtiter plate are coated with 200 nanograms (50 microliters per well) of rabbit IgG anti-HSV diluted in carbonate-bicarbonate buffer (pH 9.5) and incubated at 4° C. overnight. Wells are postcoated with 0.5% gelatin-PBS (200 microliters per well) and incubated for 30 minutes at 22° C. The wells are washed once with 0.01% gelatin-PBS (200 microliters per well). Samples to be tested are added (50 microliters per well) and incubated for 2 hours at 45° C. (water bath). The wells are washed three times with 0.01% gelatin-PBS and biotinylated monoclonal antibody diluted in 0.1% gelatin-PBS is added to the wells and incubated for one hour at 37° C. (water bath). The wells are then washed three times with 0.01% gelatin-PBS and avidin-diluted in 0.1% gelatin-PBS is added to the wells and incubated for 20 minutes at 22° C. The wells are washed three times with 0.1% gelatin-PBS, biotinylated alkaline phosphatase diluted in 0.1% gelatin-PBS is then added to the wells and incubated for 20 minutes at 22° C. The wells are washed three times with 0.01% gelatin-PBS. The substrate is added to the wells (200 microliters per well) and absorbancy monitored at 405 nm.

EXAMPLE 5

With reference to FIG. 4, a distinct alternative embodiment of the invention comprises forming a matrix comprising antibody against human IgM immunoglobulin and contacting the resultant matrix with a sample suspected of containing IgM immunoglobulin reactive with HSV. The matrix is separated from the supernatant and then contacted with biotin labeled HSV antigen, the latter in a pre-determined effective amount. The matrix is again separated from the supernatant and contacted with a readably labeled avidin to bind to the biotin if present in the matrix. The matrix is again separated from the supernatant and the label, if present in the matrix, read to quantitatively or qualitatively determine the presence of IgM immunoglobulin reacted with HSV sought in the sample.

Preparation of biotin labeled virus antigen, preparation of antibody against IgM immunoglobulin In a manner within the general description set forth above, 200 nanograms in 50 microliters of an affinity-purified IgG preparation of goat antibody specific for the mu heavy chain of human IgM was absorbed on the surface of a polystyrene 96 well microtiter plate in carbonate-bicarbonate buffer (pH 9.5) for eight hours at 4° C. After blocking with a 10% FCS, a 1:200 dilution of the patient's serum in PBS/0.1% gelatin (50 microliters volume) was added and incubated for one hour at 37° C. (water bath). Excess antibody was removed by washing three times with Tween 20-PBS. A 1:25 dilution of equal numbers of particles of HSV1 and HSV2 antigens that had been biotinylated similarly to the protocol previously described was added and incubated for 2 hours at 37° C. (water bath). After washing three times with Tween 20-PBS, a 1:25 dilution of avidin alkaline phosphatase was added and incubated for 20 minutes at room temperature. The wells were washed three times with Tween 20-PBS. Substrate was added and adsorbancy was monitored at 405 nm. To demonstrate the efficacy of the test, sample serums were introduced into the above-described process as samples to be determined. The results were as follows:

| Serum Source | OD$_{405}$ |
| --- | --- |
| Clinically normal human serum | 0.18 (0.04)* |
| Clinically IgM anti-HSV1 | 0.66 (0.07) |
| Clinically IgG anti-HSV2 | 0.21 (0.05) |
| Clinically IgM anti-HSV2 | 0.45 (0.03) |

*standard deviation

Another aspect of this invention are diagnostic packs useful for performing the assay described above, e.g.:

A diagnostic pack for the demonstration and determination of a herpes simplex virus antigen which comprises:
(a) A given quantity of a matrix coated with anti-herpes simplex virus IgG derived from a host distinct from the host used to produce the monoclonal antibody also present in the pack.
(b) A corresponding given quantity of monoclonal IgM antibody specific against herpes simplex virus.
(c) A corresponding given quantity of avidin linked enzyme.
(d) A substrate for the determination of the enzyme activity of said enzyme.

A diagnostic pack for the demonstration and determination of a herpes simplex virus antigen which comprises:
(a) A given quantity of a matrix coated with anti-herpes simplex virus IgG derived from a host distinct from the host used to produce the monoclonal antibody also present in the pack.
(b) A corresponding given quantity of monoclonal IgM antibody against herpes simplex virus.
(c) A corresponding given quality of biotinylated (i) antibody against said monoclonal antibody derived from a host distinct from the host used to produce said monoclonal antibody, or (ii) Fab' fragment of (i) reactive against said monoclonal antibody.
(d) A corresponding given quantity of avidin linked enzyme.
(e) A substrate for the determination of the enzyme activity of said enzyme.

A diagnostic pack for the demonstration and determination of a herpes simplex virus antigen which comprises:
(a) A given quantity of a matrix coated with anti-herpes simplex virus IgG derived from a lot distinct from the lot used to produce the monoclonal antibody also present in the pack.
(b) A corresponding given quantity of biotinylated monoclonal IgM antibody specific against herpes simplex virus.
(c) A corresponding given quantity of avidin.
(d) A corresponding given quantity of avidin linked enzyme.
(e) A substrate for the determination of the enzyme activity of said enzyme.

A diagnostic pack for the demonstration and determination of IgM specific to herpes simplex virus antigen which comprises:
- (a) A given quantity of a matrix coated with anti-human IgM heavy chain specific antibody.
- (b) A corresponding given quantity of biotinylated herpes simplex virus.
- (c) A corresponding given quantity of avidin linked enzyme.
- (d) A substrate for the determination of the enzyme activity of said enzyme.

What is claimed is:

1. An immunoassay which comprises:
   a. forming an insoluble matrix comprising IgG antibody against a virus antigen to be detected;
   b. contacting said matrix with a biological fluid to immunocapture the virus antigen sought to be detected;
   c. contacting the resultant matrix with a biotin labeled monoclonal IgM antibody against said virus antigen;
   d. contacting the resultant matrix with readably labeled avidin; and
   e. determining the presence of and/or quantifying the immunocaptured virus antigen from the biological fluid by reading the labeled avidin immunocaptured by the matrix.

2. A diagnostic pack for the demonstration and determination of a herpes simplex virus antigen which comprises:
   a. a given quantity of a matrix coated with anti-herpes simplex virus IgG derived from a host distinct from the host used to produce the biotin labeled monoclonal antibody also present in the pack;
   b. a corresponding given quantity of biotin labeled monoclonal IgM antibody specific against herpes simplex virus;
   c. a corresponding given quantity of avidin linked enzyme; and
   d. a substrate for the determination of the enzyme activity of said enzyme.

3. The diagnostic pack of claim 2 where (a) is rabbit derived IgG and (b) is mouse derived biotin labeled monoclonal IgM.

4. An immunoassay which comprises:
   a. forming an insoluble matrix comprising IgG antibody against a virus antigen to be detected;
   b. contacting said matrix with a biological fluid to immunocapture the virus antigen sought to be detected;
   c. contacting the resultant matrix with monoclonal IgM antibody against said virus antigen;
   d. contacting the resultant matrix with a biotin labeled antibody against said monoclonal antibody;
   e. contacting the resultant matrix with readably labeled avidin; and
   f. determining the presence of and/or quantifying the immunocaptured virus antigen from the biological fluid by reading the labeled avidin immunocaptured by the matrix.

5. A diagnostic pack for the demonstration and determination of a herpes simplex virus antigen which comprises:
   a. a given quantity of a matrix coated with anti-herpes simplex virus IgG derived from a host distinct from the host used to produce the monoclonal IgM antibody also present in the pack;
   b. a corresponding given quantity of monoclonal IgM antibody against herpes simplex virus;
   c. a corresponding given quantity of biotinylated (i) antibody against said monoclonal antibody derived from a host distinct from the host used to produce said monoclonal antibody, or (ii) biotinylated Fab' fragment of (i) reactive against said monoclonal antibody;
   d. a corresponding given quantity of avidin linked enzyme; and
   e. a substrate for the determination of the enzyme activity of said enzyme.

6. The diagnostic pack as in claim 5 wherein (a) is rabbit derived IgG and (b) is mouse derived monoclonal IgM.

7. An immunoassay which comprises:
   a. forming an insoluble matrix comprising IgG antibody against a virus antigen to be detected;
   b. contacting said matrix with a biological fluid to immunocapture the virus antigen sought to be detected;
   c. contacting the resultant matrix with biotin labeled monoclonal antibody against said virus antigen;
   d. contacting the resultant matrix with avidin;
   e. contacting the resultant matrix with a readably labeled biotin; and
   f. determining the presence of and/or quantifying the immunocaptured virus antigen from the biological fluid by reading the labeled biotin immunocaptured by the matrix.

8. A diagnostic pack for the demonstration and determination of a herpes simplex virus antigen which comprises:
   a. a given quantity of a matrix coated with anti-herpes simplex virus IgG derived from a host distinct from the host used to produce the monoclonal antibody also present in the pack;
   b. a corresponding given quantity of biotinylated monoclonal IgM antibody specific against herpes simplex virus;
   c. a corresponding given quantity of avidin;
   d. a corresponding given quantity of avidin linked enzyme; and
   e. a substrate for the determination of the enzyme activity of said enzyme.

9. The diagnostic pack of claim 8 wherein (a) is rabbit derived IgG and (b) is mouse derived monoclonal biotinylated IgM.

10. An immunoassay which comprises:
    a. forming an insoluble matrix comprising anti-human IgM antibody;
    b. contacting said matrix with a biological fluid to immunocapture IgM immunoglobulin sought to be detected;
    c. contacting the resultant matrix with biotin labeled virus antigen, which virus is a virus which combines with the IgM immunoglobulin sought to be detected;
    d. contacting the resultant matrix with readably labeled avidin; and
    e. determining the presence of and/or quantifying the immunocaptured IgM immunoglobulin from the biological fluid by reading the labeled avidin immunocaptured by the matrix.

11. A diagnostic pack for the demonstration and determination of IgM specific to herpes simplex virus antigen which comprises:

a. a given quantity of a matrix coated with anti-human IgM antibody;
b. a corresponding given quantity of biotinylated herpes simplex virus;
c. a corresponding given quantity of avidin linked enzyme; and
d. a substrate for the determination fo the enzyme activity of said enzyme.

12. The diagnostic pack as in claim 11 wherein (a) is goat anti-human IgM antibody.

13. The assay of claims 1, 4, 7 or 10 wherein the readable label is an enzyme which is contacted with a reactive substrate.

14. The assays of claims 1, 4, 7 or 10 where the virus antigen is herpes simplex virus antigen.

15. The assay of claim 13 where the virus antigen is herpes simplex virus antigen.

16. In an immunoassay for the detection of herpes simplex virus wherein an antibody to herpes simplex is introduced, the improvement comprising introducing as said antibody a monoclonal IgM antibody against herpes simplex virus.

17. The immunoassay of claim 16, wherein the virus is HSV1.

18. The immunoassay of claim 16, wherein the virus is HSV2.

* * * * *